United States Patent [19]
Chenchik et al.

[11] Patent Number: 6,077,673
[45] Date of Patent: Jun. 20, 2000

[54] MOUSE ARRAYS AND KITS COMPRISING THE SAME

[75] Inventors: Alex Chenchik, Palo Alto, Calif.; Matvey Lukashev, Newton, Mass.

[73] Assignee: Clontech Laboratories, Inc., Palo Alto, Calif.

[21] Appl. No.: 09/222,248

[22] Filed: Dec. 28, 1998

Related U.S. Application Data

[63] Continuation-in-part of application No. 09/053,375, Mar. 31, 1998.

[51] Int. Cl.$^7$ .................................................. C12Q 1/68
[52] U.S. Cl. ........................... 435/6; 422/68.1; 435/283.1; 435/285.1; 435/286.1; 435/286.2; 435/287.1; 435/287.2; 435/287.7; 435/287.9; 435/289.1; 435/299.1
[58] Field of Search ................. 422/50, 68.1; 435/283.1, 435/285.1, 286.1, 286.2, 287.1, 287.2, 287.7, 287.9, 289.1, 299.1, 6

[56] References Cited

U.S. PATENT DOCUMENTS

| | | | |
|---|---|---|---|
| 5,436,327 | 7/1995 | Southern et al. | 536/25.34 |
| 5,445,934 | 8/1995 | Fodor et al. | 435/6 |
| 5,556,752 | 9/1996 | Lockhart et al. | 435/6 |
| 5,700,637 | 12/1997 | Southern | 435/6 |
| 5,723,320 | 3/1998 | Dehlinger | 435/91.1 |
| 5,800,992 | 9/1998 | Fodor et al. | 435/6 |
| 5,830,645 | 11/1998 | Pinkel et al. | 435/6 |

FOREIGN PATENT DOCUMENTS

| | | | |
|---|---|---|---|
| 0 373 203 B1 | 8/1994 | European Pat. Off. | C12Q 1/68 |
| 0 742 287 A2 | 11/1996 | European Pat. Off. | C12Q 1/68 |
| 90/10716 | 9/1990 | WIPO | C12Q 1/68 |
| 93/17126 | 9/1993 | WIPO | C12Q 1/68 |
| 95/11995 | 5/1995 | WIPO | C12Q 1/68 |
| 95/35505 | 12/1995 | WIPO | G01N 33/543 |

OTHER PUBLICATIONS

Stratagene 1988 Catalog (Published by Stratagene, LaJolla, CA), p. 39, 1988.
Chalifour, Lorraine E., et al., "A Method for Analysis of Gene Expression Patterns," *Analytical Biochemistry* (1994) vol. 216:299–304.
DeRisi, Joseph L. et al., "Exploring the Metabolic and Genetic Control of Gene Expression on a Genomic Scale," *Science* (Oct. 24, 1997) vol. 278:680–686.
Ehlers, Stefan, et al., "Differentiation of T Cell Lymphokine Gene Expression: The In Vitro Acquisition of T Cell Memory," *J. Exp. Med.* (Jan. 1991) vol. 173:25–36.
Glaser, Vicki, "Rosetta Impharmatics Chips In," *Nature Biotechnology* (Oct. 1997) vol. 15:937–938.
Goodwin, Raymond G., et al., "Cloning of the Human and Murine Interlukin–7 Receptors: Demonstration of a Soluble, Form and Homology to a New Receptor Superfamily," *Cell* (Mar. 23, 1990) vol. 60:941–951.
Goodwin, Raymond G., et al., "Human Interleukin 7: Molecular Cloning and Growth Factor Activity on Human and Murine B–Lineage Cells," *Proc. Natl. Acad. Sci. USA* (Jan. 1989) vol. 86:302–306.
Hoheisel, Jorg D., "Oligomer–chip Technology," *Tibtech* (Nov. 1997)vol. 15:465–469.
Leonard, Warren J., et al., "Molecular Cloning and Expression of cDNAs for the Human Interleukin–2 Receptor," *Nature* (Oct. 1984) vol. 311:626–631.
Lockhart, David J., et al., "Expression Monitoring by Hybridization to High–Density Oligonucleotide Arrays," *Nature Biotechnology* (Dec. 1996) vol. 14:1675–1680.
Marshall, Andrew, et al., "DNA Chips: An Array of Possibilities," *Nature Biotechnology* (Jan. 1998) vol. 16:27–31.
Nishi, Tatsunari et al., "Cloning and Expression of a Novel Variant of Human Interferon–γ cDNA," *J. Biochem* (1985) vol. 97:153–159.
Nguyen, Catherine, et al., "Differential Gene Expression in the Murine Thymus Assayed by Quantitative Hybridization of Arrayed cDNA Clones," *Genomics* (1995) vol. 29:207–216.
Ramsay, Graham, "DNA Chips: State–of–the–art," *Nature Biotechnology* (Jan. 1998) vol. 16:40–44.
Schena, Mark, et al., "Parallel Human Genome Analysis: Microarray–Based Expression Monitoring of 1000 Genes," *Proc. Natl. Acad. Sci. USA* (Oct. 1996) vol. 93:10614–10619.
Shalon, Dari, et al., "A DNA Microarray System for Analyzing Complex DNA Samples Using Two–color Fluorescent Probe Hybridization," *Genome Research* (1996) vol. 6:639–645.
"Atlas Human cDNA Expression Array 1," *CLONTECHniques* XII (Apr. 1997) vol. 2:76–78.
Zhao, Nanding, et al., "High–Density cDNA Filter Analysis: A Novel Approach for Large–Scale, Quantitative Analysis of Gene Expression," *Gene* (1995) vol. 156:207–213.

*Primary Examiner*—Ardin H. Marschel
*Attorney, Agent, or Firm*—Bret E. Field; Bozicevic, Field & Framcis, LLP

[57] ABSTRACT

Mouse arrays and methods for their use are provided. The subject arrays include a plurality of polynucleotide spots, each of which is made up of a polynucleotide probe composition of unique polynucleotides corresponding to a key mouse gene. The subject arrays find use in hybridization assays, particularly in assays for the identification of differential gene expression of key mouse genes of interest.

17 Claims, No Drawings

MOUSE ARRAYS AND KITS COMPRISING THE SAME

CROSS-REFERENCE TO RELATED APPLICATIONS

This application is a continuation-in-part of application Ser. No. 09/053,375 filed on Mar. 31, 1998, the disclosure of which is herein incorporated by reference.

INTRODUCTION

1. Technical Field

The field of this invention is biopolymeric arrays.

2. Background of the Invention

"Biochips" or arrays of binding agents, such as oligonucleotides and peptides, have become an increasingly important tool in the biotechnology industry and related fields. These binding agent arrays, in which a plurality of binding agents are deposited onto a solid support surface in the form of an array or pattern, find use in a variety of applications, including drug screening, nucleic acid sequencing, mutation analysis, and the like. One important use of biochips is in the analysis of differential gene expression, where the expression of genes in different cells, normally a cell of interest and a control, is compared and any discrepancies in expression are identified. In such assays, the presence of discrepancies indicates a difference in the classes of genes expressed in the cells being compared.

In methods of differential gene expression, arrays find use by serving as a substrate to which is bound nucleic acid "probe" fragments. One then obtains "targets" from analogous cells, tissues or organs of a healthy and diseased organism. The targets are then hybridized to the immobilized set of nucleic acid "probe" fragments. Differences between the resultant hybridization patterns are then detected and related to differences in gene expression in the two sources.

A variety of different array technologies have been developed in order to meet the growing need of the biotechnology industry, as evidenced by the extensive number of patents and references listed in the relevant literature section below.

Despite the wide variety of array technologies currently in preparation or available on the market, there is a continued need to identify new array devices to meet the needs of specific research applications.

Relevant Literature

Patents and patent applications describing arrays of biopolymeric compounds and methods for their fabrication include: U.S. Pat. Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,895; 5,624,711; 5,639,603; 5,658,734; 5,700,637; 5,744,305; 5,770,456; WO 93/17126; WO 95/11995; WO 95/35505; EP 742 287; and EP 799 897.

Patents and patent application describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; WO 95/21265; WO 96/31622; WO 97/10365; WO 97/27317; EP 373 203; and EP 785 280.

Other references of interest include: Atlas Human cDNA Expression Array I (April 1997) CLONTECHniques XII: 4–7; Lockhart et al., Nature Biotechnology (1996) 14: 1675–1680; Shena et al., Science (1995) 270: 467–470; Schena et al., Proc. Nat'l Acad. Sci. USA (1996) 93:10614–10619; Shalon et al., Genome Res. (1996) 6: 639–645; Milosavljevic et al., Genome Res. (1996) 6:132–141; Nguyen et al., Genomics (1995)29: 207–216; Pietu et al., Genome Res. (1996) 6: 492–503; Zhao et al., Gene (1995) 166:207–213; Chalifour et al., Anal. Biochem. (1994) 216:299–304; Heller et al., Proc. Nat'l Acad. Sci. USA (1997) 94: 2150–2155; and Schena, M., BioAssays (1996) 18: 427–431.

SUMMARY OF THE INVENTION

Mouse arrays and kits including the same, as well as methods for their preparation and use in hybridization assays, are provided. The subject arrays have a plurality of probe polynucleotide spots each made up of a unique polynucleotide(s) that corresponds to a key mouse gene of interest. The subject arrays find use in the expression analysis of key mouse genes.

DEFINITIONS

The term "nucleic acid" as used herein means a polymer composed of nucleotides, e.g. deoxyribonucleotides or ribonucleotides.

The terms "ribonucleic acid" and "RNA" as used herein means a polymer composed of ribonucleotides.

The terms "deoxyribonucleic acid" and "DNA" as used herein means a polymer composed of deoxyribonucleotides.

The term "oligonucleotide" as used herein denotes single stranded nucleotide multimers of from about 10 to 100 nucleotides in length.

The term "polynucleotide" as used herein refers to single or double stranded polymer composed of nucleotide monomers of greater than about 120 nucleotides in length up to about 1000 nucleotides in length.

"Key mouse genes" and "key mouse related genes" are those genes that have been identified by those of skill in the art to play primary roles in a variety of different biological processes. Typically the mouse genes represented on the array are genes that are under tight transcriptional control. Key mouse genes of interest that may be represented on the array include: oncogenes, cell cycle genes, apoptosis genes, growth factor genes, cytokine genes, interleukin genes, receptor genes, and genes associated with different stages of embryonic development. Preferably, the key mouse genes are genes that are well characterized, i.e. at least genes in which at least the partial sequence is known and the function of the expression product of the gene is at least partially understood. Specific key mouse genes of interest include those listed in Table 1, infra. A gene is considered to be the same as a gene listed in Table 1 even if it: (a) has a different name or accession number in a gene sequence database, e.g. GENBANK; (b) has at least 90% homology (as determined using the FASTA program with default settings) to the sequence of one of the GENBANK accession numbers listed in Table 1; or (c) belongs to the same gene cluster as defined in NCBI in Unigene database available on the World Wide Web.

The "unique" polynucleotide sequences of each probe spot on the arrays of the subject invention are distinctive or different with respect to every other unique polynucleotide sequence on the arrays that corresponds to a key mouse gene, as that term is defined herein. In other words, for at least 80% of the genes on the array, and more usually at least 90% of the genes on the array, any two different unique polynucleotides corresponding to a key mouse gene on the array, (i.e. any two unique polynucleotides taken from different, non-identical spots on the array), are not homologous. By not homologous is meant that the sequence identity between the two given unique polynucleotides is less than about 90%, usually less than about 85% and more usually less than about 80% as measured by the FASTA program using default settings. Moreover, each polynucleotide sequence on the array is statistically chosen to ensure that the probability of homology to any sequence of that type is very low. Morever, each unique sequence on the array is statistically chosen to insure that probability of homology to any other known sequence associated with key mouse genes is very low, whether or not the other sequence is represented on the array. An important feature of the individual polynucleotide probe compositions of the subject arrays is that they are only a fragment of the entire cDNA of the key mouse gene to which they correspond. In other words, for each gene represented on the array, the entire cDNA sequence of the gene is not represented on the array. Instead, the sequence of only a portion or fragment of the entire cDNA is represented on the array by this unique polynucleotide.

The term "polynucleotide probe composition" refers to the nucleic acid composition that makes up each of the probe spots on the array that correspond to a particular key mouse gene. Thus, the term 'polynucleotide probe composition' includes nucleic acid compositions of unique polynucleotides but excludes control or calibrating polynucleotides (e.g. polynucleotides corresponding to housekeeping genes) which may also be present on the array, as described in greater detail infra. The polynucleotide compositions are made up of single stranded polynucleotides (i.e. polynucleotides that are not hybridized to each other), where all of the polynucleotides in the probe composition may be identical to each other or there may be two or more different polynucleotides (i.e. polynucleotides of different nucleotide sequence) in each probe composition, e.g. where the two different polynucleotides are complementary to each other.

DESCRIPTION OF THE SPECIFIC EMBODIMENTS

Mouse arrays, as well as methods for their preparation and use, are provided. In the subject mouse arrays, a plurality of polynucleotide probe spots is stably associated with the surface of a solid support. Each different polynucleotide probe spot is made up of a unique polynucleotide that corresponds to a key mouse gene of interest. The subject arrays find particular use in gene expression assays of key mouse genes. In further describing the subject invention, the mouse arrays themselves are first discussed, followed by a description of methods for their preparation. Next, a review of representative applications in which the subject arrays may be employed is provided.

It is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Arrays of the Subject Invention-General Description

Array Structure

The arrays of the subject invention have a plurality of polynucleotide probe spots stably associated with a surface of a solid support. Each probe spot on the array comprises a polynucleotide probe sample or polynucleotide probe composition of known identity, usually of known sequence, as described in greater detail below. The polynucleotide probe spots on the array may be any convenient shape, but will typically be circular, elliptoid, oval, annular, or some other analogously curved shape, where the shape may, in certain embodiments, be a result of the particular method employed to produce the array. The density of the all of the spots on the solid surface, i.e. both probe spots and non-probe spots, e.g. calibration spots, control spots, etc., is at least about $5/cm^2$ and usually at least about $10/cm^2$ but does not exceed about $1000/cm^2$, and in many embodiments does not exceed about $500/cm^2$, where in certain preferred embodiments, the density does not exceed about $400/cm^2$, usually does not exceed about $300/cm^2$, and more usually does not exceed about $60/cm^2$. The spots may be arranged in any convenient pattern across or over the surface of the array, such as in rows and columns so as to form a grid, in a circular pattern, and the like, where generally the pattern of spots will be present in the form of a grid across the surface of the solid support.

In the subject arrays, the spots of the pattern are stably associated with the surface of a solid support, where the support may be a flexible or rigid solid support. By stably associated is meant that the polynucleotides of the spots maintain their position relative to the solid support under hybridization and washing conditions. As such, the polynucleotide members which make up the spots can be non-covalently or covalently stably associated with the support surface. Examples of non-covalent association include non-specific adsorption, binding based on electrostatic (e.g. ion, ion pair interactions), hydrophobic interactions, hydrogen bonding interactions, specific binding through a specific binding pair member covalently attached to the support surface, and the like. Examples of covalent binding include covalent bonds formed between the spot polynucleotides and a functional group present on the surface of the rigid support, e.g. —OH, where the functional group may be naturally occurring or present as a member of an introduced linking group, as described in greater detail below.

The array is present on either a flexible or rigid substrate. By flexible is meant that the support is capable of being bent, folded or similarly manipulated without breakage. Examples of solid materials which are flexible solid supports with respect to the present invention include membranes, flexible plastic films, and the like. By rigid is meant that the support is solid and does not readily bend, i.e. the support is not flexible. As such, the rigid substrates of the subject arrays are sufficient to provide physical support and structure to the polymeric targets present thereon under the assay conditions in which the array is employed, particularly under high throughput handling conditions. Furthermore, when the rigid supports of the subject invention are bent, they are prone to breakage.

The solid supports upon which the subject patterns of spots are present in the subject arrays may take a variety of configurations ranging from simple to complex, depending on the intended use of the array. Thus, the substrate could have an overall slide or plate configuration, such as a rectangular or disc configuration. In many embodiments, the substrate will have a rectangular cross-sectional shape, having a length of from about 10 mm to 200 mm, usually from about 40 to 150 mm and more usually from about 75 to 125 mm and a width of from about 10 mm to 200 mm, usually from about 20 mm to 120 mm and more usually from about 25 to 80 mm, and a thickness of from about 0.01 mm to 5.0 mm, usually from about 0.1 mm to 2 mm and more usually from about 0.2 to 1 mm.

The substrates of the subject arrays may be fabricated from a variety of materials. The materials from which the substrate is fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, is of particular interest in this embodiment. For rigid substrates, specific materials of interest include: glass; plastics, e.g. polytetrafluoroethylene, polypropylene, polystyrene, polycarbonate, and blends thereof, and the like; metals, e.g. gold, platinum, and the like; etc.

The substrates of the subject arrays comprise at least one surface on which the pattern of probe spots is present, where the surface may be smooth or substantially planar, or have irregularities, such as depressions or elevations. The surface on which the pattern of spots is present may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof, e.g. peptide nucleic acids and the like; polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto, e.g. conjugated.

The total number of probe spots on the substrate will vary depending on the number of different polynucleotide probes one wishes to display on the surface, as may be desired depending on the particular application in which the subject arrays are to be employed. Generally, the pattern present on the surface of the array will comprise at least about 10 distinct spots, usually at least about 20 distinct spots, and more usually at least about 50 distinct spots, where the number of spots may be as high as 10,000 or higher, but will usually not exceed about 5,000 distinct spots, and more usually will not exceed about 3,000 distinct spots. In many embodiments, it is preferable to have each distinct probe composition presented in duplicate, i.e. so that there are two spots for each distinct polynucleotide probe composition of the array. In certain embodiments, the number of spots will range from about 400 to 1200, usually from 500 to 1200.

In the arrays of the subject invention (particularly those designed for use in high throughput applications, such as high throughput analysis applications), a single pattern of spots may be present on the array or the array may comprise a plurality of different spot patterns, each pattern being as defined above. When a plurality of different spot patterns are present, the patterns may be identical to each other, such that the array comprises two or more identical spot patterns on its surface, or the spot patterns may be different, e.g. in arrays that have two or more different types of target nucleic acids represented on their surface, e.g an array that has a pattern of spots corresponding to key mouse genes and a pattern of spots corresponding to another type or category of mouse genes, such as mouse stress genes. Where a plurality of spot patterns are present on the array, the number of different spot patterns is at least 2, usually at least 6, more usually at least 24 or 96, where the number of different patterns will generally not exceed about 384.

Where the array comprises a plurality of spot patterns on its surface, preferably the array comprises a plurality of reaction chambers, wherein each chamber has a bottom surface having associated therewith an pattern of spots and at least one wall, usually a plurality of walls surrounding the bottom surface. Such array configurations and the preparation thereof is further described in U.S. patent application Ser. No. 08/974,298 filed on Nov. 19, 1997, the disclosure of which is herein incorporated by reference. Of particular interest in many embodiments are arrays in which the same pattern of spots in reproduced in 24 or 96 different reaction chambers across the surface of the array.

Within any given pattern of spots on the array, there may be a single spot that corresponds to a given target or a number of different spots that correspond to the same target, where when a plurality of different spots are present that correspond to the same target, the probe compositions of each spot that corresponds to the same target may be identical of different. In other words, a plurality of different targets are represented in the pattern of spots, where each target may correspond to a single spot or a plurality of spots, where the probe composition among the plurality of spots corresponding to the same target may be the same or different. Where a plurality of spots (of the same or different composition) corresponding to the same target is present on the array, the number of spots in this plurality will be at least about 2 and may be as high as 10, but will usually not exceed about 5. The number of different targets represented on the array is at least about 2, usually at least about 10 and more usually at least about 20, where in many embodiments the number of different targets, e.g. genes, represented on the array is at least about 50. The number of different targets represented on the array may be as high as 1000 or higher, but will usually not exceed about 800 and more usually will not exceed about 700. In a preferred embodiment, the number of different targets represented on the array ranges from about 400 to 800, an usually from about 500 to 7000. A target is considered to be represented on an array if it is able to hybridize to one or more probe compositions on the array.

The amount of polynucleotide present in each spot will be sufficient to provide for adequate hybridization and detection of target nucleic acid during the assay in which the array is employed. Generally, the amount of polynucleotide in each spot will be at least about 0.1 ng, usually at least about 0.5 ng and more usually at least about 1 ng, where the amount may be as high as 1000 ng or higher, but will usually not exceed about 20 ng and more usually will not exceed about 10 ng. The copy number of each polynucleotide in a spot will be sufficient to provide enough hybridization sites for target molecule to yield a detectable signal, and will generally range from about 0.01 fmol to 50 fmol, usually from about 0.05 fmol to 20 fmol and more usually from about 0.1 fmol to 5 fmol. Where the spot has an overall circular dimension, the diameter of the spot will generally range from about 10 to 5,000 $\mu$m, usually from about 20 to 2,000 $\mu$m and more usually from about 50 to 1000 $\mu$m.

A critical feature of the subject arrays is that all of the probe polynucleotide spots of the array correspond to key mouse genes of interest, particularly genes that have been identified by those of skill in the art to play primary roles in a variety of different biological processes of the mouse. Typically the mouse genes represented on the array are genes that are under tight transcriptional control. As such, each polynucleotide probe spot on the array will correspond to a key mouse gene of interest. Each probe spot on the array may correspond to a different key mouse gene. Alternatively, two or more, usually no more than four, and more usually no more than three, different probe spots may correspond to the same key mouse gene, i.e. a key mouse gene may be represented by one or a plurality of different probe spots on the array. Furthermore, any given key mouse gene may be represented by two or more identical probe spots on the array, e.g. a particular probe spot may be presented on the array once or in duplicate, triplicate, etc, as mentioned above. The number of different key mouse genes represented on the array may vary, where generally the number of different key mouse genes represented on the array will range from about 50 to 1000, usually from about 100 to 700 and more usually from about 300 to 700. A key mouse gene is considered to be represented on a given array if a target nucleic acid derived from the key mouse gene is able to hybridize to at least one probe spot on the array. Key mouse genes that may be represented on the arrays include: oncogenes, cell cycle genes, apoptosis genes, growth factor genes, cytokine genes, interleukin genes, receptor genes, genes associated with different stages of embryonic development, and the like. In certain embodiments, of particular interest is an array having the following types of genes represented on its surface: oncogenes & tumor suppressors; cell cycle regulators; stress response proteins; ion channel & transport proteins; intracellular signal transduction modulators & effectors; apoptosis-related proteins; DNA synthesis, repair & recombination proteins; transcription factors & general DNA binding proteins; growth factor & chemokine receptors; interleukin & interferon receptors, hormone receptors; neurotransmitter receptors; cell-surface antigens & cell adhesion proteins; interleukins & interferons; cytoskeleton & motility proteins; and protein turnover. Specific key mouse genes that may be represented on the arrays of the subject invention include those listed in Table 1, infra. In many preferred embodiments, the subject mouse arrays will include at least 20, usually at least 50 and more usually at least 100 of the genes listed in Table 1 (i.e. at least 20, usually at least 50 and more usually at least 100 of the genes listed in Table 1 are represented on the array), where in certain preferred embodiments, all of the genes listed in Table 1 are present on the array. In a particularly preferred embodiment, the array is made up of polynucleotide probes having a sequence that is identical to and/or complementary to, or at least partially includes, each of the specific gene regions listed in Col. 3 of Table 1.

The average length of the probe polynucleotides on the array is chosen to be of sufficient length to provide a strong and reproducible signal, as well as tight and robust hybridization. As such, the average length of the polynucleotides of the array will typically range from about 120 to 1000 nt and usually from about 150 to 800 nt, where in many embodiments, the average length ranges from about 200 to 700 nt, and usually 200 to 600 nt. The length of each polynucleotide on the array is less than the length of the mRNA to which it corresponds. As such, the polynucleotide represents only a fraction of the full length cDNA to which it corresponds.

The polynucleotide probe compositions that make up each spot on the array will be substantially, usually completely, free of non-nucleic acids, i.e. the probe compositions will not comprise non-nucleic acid biomolecules found in cells, such as proteins, lipids, and polysaccharides. In other words, the oligonucleotide spots of the arrays are substantially, if not entirely, free of non-nucleic acid cellular constituents. By substantially free is meant that the probe composition is at least about 90%, usually at least about 95% and more usually at least about 98% dry weight nucleic acid.

The polynucleotide probes may be nucleic acid, e.g. RNA, DNA, or nucleic acid mimetics, e.g. such as nucleic acids comprising non-naturally occurring heterocyclic nitrogenous bases, peptide-nucleic acids, locked nucleic acids (see Singh & Wengel, Chem. Commun. (1998) 1247–1248); and the like. Nucleic acid mimetics that may be polynucleotide probes on the present arrays include nucleic acids chemically modified from the native phosphodiester structure in order to increase their intracellular stability and binding affinity. A number of such modifications have been described in the literature which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As mentioned above, the subject arrays typically comprise one or more additional spots of polynucleotides which are not key mouse genes. Other spots which may be present on the substrate surface include spots comprising genomic DNA, housekeeping genes, negative and positive control genes, and the like. These latter types of spots comprise polynucleotides that are not "unique" as that term is defined and used herein, i.e. they are "common." In other words, they are calibrating or control genes whose function is not to tell whether a particular "key" mouse gene of interest is expressed, i.e. whether a particular key mouse gene is expressed in a particular sample, but rather to provide other useful information, such as background or basal level of expression, and the like. For example, spots comprising genomic DNA may be provided in the array, where such spots may serve as orientation marks. Spots comprising plasmid and bacteriophage genes, genes from the same or another species which are not expressed and do not cross hybridize with the cDNA target, and the like, may be present and serve as negative controls. Specific negative controls of interest include: M13 mp18(+) strand DNA, lambda DNA and pUC 18. In addition, spots comprising housekeeping genes and other control genes from the same or another species may be present, which spots serve in the normalization of mRNA abundance and standardization of hybridization signal intensity in the sample assayed with the array. Specific housekeeping genes of interest include: ubiquitin, phospholipase A2, hypoxanthine-guanine phosphoribosyl transferase, glyceraldehyde 3-phosphate dehydrogenase, tubulina alpha, HLA class I histocompatibility antigen, C-4 alpha chain, beta-actin, 23 kDa highly basic protein and ribosomal protein S9.

Polynucleotide Probes of the Arrays

Each probe spot of the pattern present on the surface of the substrate is made up of a unique polynucleotide probe composition. By "polynucleotide probe composition" is meant a collection or population of single stranded polynucleotides capable of participating in a hybridization event under appropriate hybridization conditions, where each of the individual polynucleotides may be the same—have the same nucleotide sequence—or have different sequences, for example the probe composition may consist of 2 different single stranded polynucleotides that are complementary to each other (i.e. the two different polynucleotides in the spot are complementary but physically separated so as to be single stranded, i.e. not hybridized to each other). In many embodiments, the probe compositions will comprise two complementary, single stranded polynucleotides.

In the polynucleotide probe compositions, the sequence of the polynucleotides are chosen so that each distinct unique polynucleotide does not cross-hybridize with any other distinct unique polynucleotide of another probe spot on the array, i.e. the polynucleotide of any other polynucleotide composition that corresponds to a key mouse gene. As such, the nucleotide sequence of each unique polynucleotide of a probe composition will have less than 90% homology, usually less than 85% homology, and more usually less than 80% homology with any other different polynucleotide of a probe composition of the array, where homology is determined by sequence analysis comparison using the FASTA program using default settings. The sequence of unique polynucleotides in the probe compositions are not conserved sequences found in a number of different genes (at least two), where a conserved sequence is defined as a stretch of from about 40 to 200 nucleotides which have at least about 90% sequence identity, where sequence identity is measured as above. The polynucleotide will generally be a deoxyribonucleic acid having a length of from about 120 to 1000, usually from 120 to 700 nt, and more usually 200 to 600 nt. The polynucleotide will not cross-hybridize with any other polynucleotide on the array under standard hybridization conditions. Again, the length of the polynucleotide will be shorter than the mRNA to which it corresponds.

Array Preparation

The subject arrays can be prepared using any convenient means. One means of preparing the subject arrays is to first synthesize the polynucleotides for each spot and then deposit the polynucleotides as a spot on the support surface. The polynucleotides may be prepared using any convenient methodology, such as automated solid phase synthesis protocols, restriction digestion of a gene fragment insert cloned into a vector, preparative PCR and like, where preparative PCR or enzymatic synthesis is preferred in view of the length and the large number of polynucleotides that must be generated for each array. In the case of automated solid phase synthesis, each polynucleotide can be represented by several overlapping or non-overlapping oligonucleotides from 10 to 100 nucleotides in length, which cover all or a partial sequence of a gene or polynucleotide. See U.S. patent application Ser. No. 60/104,179, the disclosure of which is herein incorporated by reference.

For preparative PCR, primers flanking either side of the portion of the gene of interest will be employed to produce amplified copy numbers of the portion of interest. Methods of performing preparative PCR are well known in the art, as summarized in PCR, Essential Techniques (Ed. J. F. Burke, John Wiley & Sons) (1996). Alternatively, if a gene fragment of interest is cloned into a vector, vector primers can be used to amplify the gene fragment of interest to produce the polynucleotide.

In determining the portion of the gene to be amplified and subsequently placed on the array, regions of the gene having a sequence unique to that gene should preferably be amplified. Different methods may be employed to choose the specific region of the gene to be amplified. Thus, one can use a random approach based on availability of a gene of interest. However, instead of using a random approach which is based on availability of a gene of interest, a rational design approach may also be employed to choose the optimal sequence for the hybridization array. Preferably, the region of the gene that is selected and amplified is chosen based on the following criteria. First, the sequence that is chosen should yield a polynucleotide that does not cross-hybridize with any other polynucleotide that is present on the array. Second, the sequence should be chosen such that the polynucleotide has a low probability of cross-hybridizing with a polynucleotide having a nucleotide sequence found in any other gene, whether or not the gene is to be represented on the array. As such, sequences that are avoided include those found in: highly expressed gene products, structural RNAs, repeated sequences found in the sample to be tested with the array and sequences found in vectors. A further consideration is to select sequences which provide for minimal or no secondary structure, structure which allows for optimal hybridization but low non-specific binding, equal or similar thermal stabilities, and optimal hybridization characteristics.

The prepared polynucleotides may be spotted on the support using any convenient methodology, including manual techniques, e.g. by micro pipette, ink jet, pins, etc., and automated protocols. See U.S. Pat. No. 5,770,151 and WO 95/35505, the disclosures of which are herein incorporated by reference, for discussions of representative ways of spotting polynucleotides on a support. Of particular interest is the use of an automated spotting device, such as the Beckman Biomek 2000 (Beckman Instruments). As mentioned above, the polynucleotide probe compositions that are spotted onto the array surface are made up of single stranded polynucleotides, where all the polynucleotides may be identical to each other or a population of complementary polynucleotides may be present in each spot.

Methods of Using the Subject Arrays

The subject arrays find use in a variety of different applications in which one is interested in detecting the occurrence of one or more binding events between target nucleic acids and probes on the array and then relating the occurrence of the binding event(s) to the presence of a target(s) in a sample, i.e. the expression of a particularkey mouse gene in a sample. In general, the device will be contacted with the sample suspected of containing the target key mouse gene under conditions sufficient for binding of any target present in the sample to a complementary polynucleotide present on the array. Generally, the sample will be a fluid sample and contact will be achieved by introduction of an appropriate volume of the fluid sample onto the array surface, where introduction can via inlet port, deposition, dipping the array into a fluid sample, and the like.

Generation of Labeled Target

Targets may be generated by methods known in the art. mRNA can be labeled and used directly as a target, or converted to a labeled cDNA target. Generally, such methods include the use of oligonucleotide primers. Primers that may be employed include oligo dT, random primers, e.g. random hexamers and gene specific primers, as described in U.S. patent application Ser. No. 08/859,998, the disclosure of which is herein incorporated by reference. Where gene specific primers are employed, the gene specific primers are preferably those primers that correspond to the different polynucleotide spots on the array. Thus, one will preferably employ gene specific primers for each different polynucleotide that is present on the array, so that if the gene is expressed in the particular cell or tissue being analyzed, labeled target will be generated from the sample for that gene. In this manner, if a particular key mouse gene present on the array is expressed in a particular sample, the appropriate target will be generated and subsequently identified.

A variety of different protocols may be used to generate the labeled target nucleic acids, as is known in the art, where such methods typically rely on the enzymatic generation of the labeled target using the initial primer. Labeled primers can be employed to generate the labeled target. Alternatively, label can be incorporated during first strand synthesis or subsequent synthesis, labeling or amplification steps in order to produce labeled target. Representative methods of producing labeled target are disclosed in U.S. patent application Ser. No. 08/859,998, the disclosure of which is herein incorporated by reference. Alternatively, the label can be introduced by chemical cDNA synthesis.

Hybridization and Detection

As mentioned above, following preparation of the target nucleic acid from the tissue or cell of interest, the labeled target nucleic acid is then contacted with the array under hybridization conditions, where such conditions can be adjusted, as desired, to provide for an optimum level of specificity in view of the particular assay being performed. Suitable hybridization conditions are well known to those of skill in the art and reviewed in Maniatis et al, supra and WO 95/21944, e.g. stringent conditions (e.g. at 50° C. or higher and 0.1XSSC (15 mM sodium chloride/01.5 mM sodium citrate). In analyzing the differences in the population of labeled target nucleic acids generated from two or more physiological sources using the arrays described above, each population of labeled target nucleic acids are separately contacted to identical probe arrays or together to the same array under conditions of hybridization, preferably under stringent hybridization conditions, such that labeled target nucleic acids hybridize to complementary probes on the substrate surface.

Where all of the target sequences comprise the same label, different arrays will be employed for each physiological source (where different could include using the same array at different times). Alternatively, where the labels of the targets are different and distinguishable for each of the different physiological sources being assayed, the opportunity arises to use the same array at the same time for each of the different target populations. Examples of distinguishable labels are well known in the art and include: two or more different emission wavelength fluorescent dyes, like Cy3 and Cy5, two or more isotopes with different energy of emission, like $^{32}p$ and $^{33}p$, light scattering particles with different scattering spectra, labels which generate signals under different treatment conditions, like temperature, pH, treatment by additional chemical agents, etc., or generate signals at different time points after treatment. Using one or more enzymes for signal generation allows for the use of an even greater variety of distinguishable labels, based on different substrate specificity of enzymes (alkaline phosphatase/peroxidase).

Following hybridization, non-hybridized labeled nucleic acid is removed from the support surface conveniently by washing, generating a pattern of hybridized nucleic acid on the substrate surface. A variety of wash solutions are known to those of skill in the art and may be used.

The resultant hybridization patterns of labeled nucleic acids may be visualized or detected in a variety of ways, with the particular manner of detection being chosen based on the particular label of the target nucleic acid, where representative detection means include scintillation counting, autoradiography, fluorescence measurement, calorimetric measurement, light emission measurement, light scattering and the like.

Following detection or visualization, the hybridization patterns may be compared to identify differences between the patterns. Where arrays in which each of the different probes corresponds to a known gene are employed, any discrepancies can be related to a differential expression of a particular gene in the physiological sources being compared.

Utility

The subject methods find use in differential mouse gene expression assays. As such, the mouse arrays of the subject invention find use in a variety of different applications, where such applications include: profiling differential gene expression in transgenic knockout mice or other experimental mouse models; investigating processes such as embryo genesis and tumorigenesis; discovering potential therapeutic and diagnostic drug targets; and the like.

Kits

Also provided are kits for performing analyte binding assays using the subject devices, where kits for carrying out differential gene expression analysis assays are preferred. Such kits according to the subject invention will at least comprise a mouse array according to the subject invention. The kits may further comprise one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, or other post synthesis labeling reagent, such as chemically active derivatives of fluorescent dyes, biotin, digoxigenin, or strept/avidin-label conjugate or antibody-label conjugate, enzymes, such as reverse transcriptases, DNA polymerases, and the like, various buffer mediums, e.g. hybridization and washing buffers, labeled target purification reagents and components, like spin columns, etc., signal generation and detection reagents, e.g streptavidin-alkaline phosphatase conjugate, chemifluorescent or chemiluminescent substrate, and the like.

The following examples are offered by way of illustration and not by way of limitation.

EXPERIMENTAL

EXAMPLE 1

Generation of Mouse cDNA array 588 cDNA fragments corresponding to 588 different mouse key genes as listed in Table 1 were amplified from quick-clone cDNA (CLONTECH) in 588 separate test tubes using a combination of sense and antisense gene-specific primers capable of amplifying the specific gene fragments of interest as specified in Table 1. Amplification was conducted in a 100-$\mu$l volume containing 2 $\mu$l of mixture of 10 Quick-clone cDNA from placenta, brain, liver, lung, leukocytes, spleen, skeletal muscle, testis, kidney and ovary (CLONTECH), 40 mM Tricine-KOH (pH 9.2 at 22° C.), 3.5 mM Mg(OAc)$_2$, 10 mM KOAc, 75 μg/ml BSA, 200 μM of each dATP, dGTP, dCTP and dTTP, 0.2 μM of each sense and antisense gene-specific primers and 2 μl of KlenTaq Polymerase mix. Temperature parameters of the PCR reactions were as follows: 1 min at 95° C. followed by 20–35 cycles of 95° C. for 15 sec and 68° C. for 2 min; followed by a 10-min final extension at 68° C. PCR products were examined on 1.2% agarose/EtBr gels in 1× TBE buffer. As a DNA size marker a 1 Kb DNA Ladder was used. ds cDNA was then precipitated by addition of a half volume of 4M ammonium acetate (about 35 μl) and 3.7 volumes of 95% ethanol (about 260 μl). After vortexing, the tube was immediately centrifuged at 14,000 r.p.m. in a microcentrifuge for 20 min. The pellet was washed with 80% ethanol without vortexing, centrifuged as above for 10 min, air dried, and dissolved in 10 μl of deionized water. Yield of ds cDNA after the amplification step was about 5 μg. The ds cDNA fragments for all 588 genes were cloned into pAtlas 1A-cloning vector (Clontech) using blunt end ligation by T4 DNA polymerase and identity of the clones was confirmed by sequence analysis. The ds cDNA inserts with the sequence corresponding 588 genes were amplified by PCR using a combination of antisense and sense gene-specific primers, as described above. The ds cDNA was denatured by adding 1 μl of 10X denaturing solution (1 M NaOH, 10 mM EDTA) and incubating at 65° C. for 20 min. All cDNA probes were transferred in 384-well plate and loaded on positively charged nylon membrane (Schleher & Schull) using 384 pin tool and Biomek 2000 (Beckman) robot.

The resultant array has 588 different key mouse genes represented on it. The specific key mouse genes represented on the array are listed in Table 1. Also provided in Table 1 is the specific region of each gene that is represented on the array. See Col. 3 of Table 1. Thus, Table 1 also provides the sequence for each polynucleotide probe on the array. For example, the array comprises a polynucleotide probe to MmRad 51, where the probe has a DNA sequence that is either complementary or identical to the sequence of the mRNA from the 855–1199 nucleotide of the sense strand counting from the 5' end of the mRNA sequence, where the entire sequence has been deposited in GENBANK under accession no. D13473 and is therefore readily available.

TABLE 1

| GENE NAME | GENBANK # | FRAGMENT LENGTH, bp (start–end) |
|---|---|---|
| MmRad51; yeast DNA repair protein Rad51 and E coli RecA homologue | DT3473 | 855–1199 |
| Interleukin-8 receptor | D17630 | 664–1022 |
| Catenin alpha | D25281 | 1276–1594 |
| BST-l; lymphocyte differentiation antigen CD38 | D31788 | 674–1014 |
| Oncostatin M | D31942 | 1017–1360 |
| CSA receptor | L05630 | 841–1165 |
| Heparin-binding EGF-like growth factor (Diphtheria toxin receptor) | L07264 | 258–673 |
| Fms-related tyrosine kinase 3 Flt3/Flk2 ligand | U04807 | 46–418 |
| CD27; lymphocyte-specific NGF receptor family member | L24495 | 596–846 |
| Fibroblast growth factor receptor Basic (b FGF-R) | M28998 | 200–583 |
| Granulocyte colony - stimulatings factor receptor | M58288 | 251–529 |
| Growth/ diffferentiation factor 1 (GDF-1) (TGF- beta family) | M62301 | 2267–2566 |
| PKC-delta; protein kinase C delta type | M69042 | 1740–2011 |

TABLE 1-continued

| GENE NAME | GENBANK # | FRAGMENT LENGTH, bp (start–end) |
|---|---|---|
| GA binding protein beta-2 chain | M74517 | 613–931 |
| CD 40L receptor(TNF receptor family) | M83312 | 417–754 |
| Fasl receptor (Fas antigen, Apo-1 antigen) | M83649 | 416–736 |
| Interleukin 12 (p40) beta chain | M86671 | 652–963 |
| Vascular endothelial growth factor (VEGF) | M95200 | 688–955 |
| Interleukin 11 (adipogenesis inhibitory factor) | U03421 | 196–475 |
| Interleukin 15 | U14332 | 605–1057 |
| LIMK; LIM serine/threonine kinase | U15159 | 1376–1699 |
| DAD-1; defender against cell death 1 | U83628 | 221–509 |
| CD 30L receptor (Lymphocyte activation antigene CD 30, Ki-1 antigene) | U25416 | 135–435 |
| Mast cell factor | U44725 | 79–417 |
| C-C cheynokine receptor (Monocyte chemoattractant protein 1 receptor (MCP-1RA) | U56819 | 965–1262 |
| Leukemia inhibitory factor (LIF) (cholinergic differentiation factor) | X06381 | 63–366 |
| Intercellular adhesion molecule-1 | X52264 | 1053–1385 |
| Interleukin-1 receptor type II | X59769 | 882–1134 |
| Corticotropin releasing factor receptor | X72305 | 1411–1748 |
| Hepatocyte growth factor (hepapoitein) | X72307 | 641–965 |
| Keratinocyte growth factor FGF-7 | Z22703 | 63–325 |
| Activin type I receptor | Z31663 | 847–1130 |
| Transcription factor TF II D | D01034 | 291–556 |
| ZO-1; Tight junction protein; discs-large family member, partially homologous to a dIg-A tumor suppressor in Drosophila/ | D14340 | 3714–4001 |
| ERCC5 excision repair protein; DNA-repair protein complementing XP-G cells (XPG) | D16306 | 1336–1639 |
| Bax; Bcl-2 heterodimerization partner and homologue | L22472 | 172–534 |
| B7-2; T lymphocyte activation antigen CD86; CD28 antigen ligand 2, B7-2 antigen; alternative CTLA4 counter-receptor | L25606 | 570–967 |
| NF2; Merlin (moesin-ezrin-radixin-like protein); shwannomin, murine neurofibromatosis type 2 susceptibility protein | L27105 | 2175–2400 |
| Pim-1 proto-oncogene | M13945 | 2713–2930 |
| Egr-1 Zn-finger regulatory protein | M20157 | 399–753 |
| PKC-alpha; protein kinase C alpha type | M25811 | 1566–1924 |
| CD44 antigen | M27129 | 789–1141 |
| T-lymphocyte activated protein | M31042 | 285–606 |
| Neuronal-cadherin (N-cadherin) | M31131 | 1212–1409 |
| ATP-dependent DNA helicase II 70 kDa subunit; thyroid Ku (p70/p80) autoantigen p70 subunit; p70 Ku) | M38700 | 274–632 |
| G13; G-alpha-13 guanine nucleotide regulatory protein | M63660 | 2057–2377 |
| Transcription factor RelB | M83380 | 1456–1728 |
| Vascular cell adhesion protein 1 | M84487 | 984–1304 |
| ERCC3 DNA repair helicase; DNA-repair protein complementing XP-B cells (XPBC) | S71186 | 1147–1444 |
| CRE-BP1; cAMP response element binding protein 1 | S76657 | 412–748 |
| XRCC1 DNA-repair protein, affecting ligation | U02887 | 900–1183 |
| Nuclear hormone receptor ROR-ALPHA-1 | U53228 | 368–675 |
| 14-3-3 protein eta | U57311 | 374–640 |
| Prothymosin alpha | X56135 | 186–455 |
| PAX-8 (paired box protein PAX 8) | X57487 | 680–1011 |
| CamK IV; Ca2/calmodulin- | X58995 | 1269–1608 |

TABLE 1-continued

| GENE NAME | GENBANK # | FRAGMENT LENGTH, bp (start–end) |
|---|---|---|
| dependent protein kinase IV (catalytic chain) | | |
| ATP-dependent DNA helicase II 80 kDa subunit; thyroid Ku (p70/p80) autoantigen p80 subunit; p80 Ku) | X66323 | 565–875 |
| Ret proto-oncogene (Papillary thyroid carcinoma-encoded protein) | X67812 | 2359–2680 |
| Nm23-M2; nucleoside diphosphate kinase B; metastasis-reducing protein;. c-myc-related transcription factor | X68193 | 80–454 |
| MAPKK6; MAP kinase kinase 6(dual specificity) (MKK6) | X97052 | 375–711 |
| DNA polymerase alpha catalytic subunit (p180) | D17384 | 563–908 |
| Caspase-3; Nedd2 cysteine protease (positive regulator of programmed cell death ICH-1 homologue) | D28492 | 398–694 |
| PSD-95/SAP90A | D50621 | 1512–1889 |
| Angiotensin-converting enzyme (ACE) (clone ACE.5.) | L04946 | 850–1113 |
| Clusterin; complement lysis inhibitor; testosterone-repressed prostate message 2; apolipoprotein J; sulfated glycoprotein-2 | L08235 | 515–744 |
| Adipocyte differentiation-associated protein | L12721 | 404–709 |
| Epidermal growth factor receptor kinase substrate EPS8 | L21671 | 1562–1873 |
| Jak3 tyrosine-protein kinase; Janus kinase 3 | L33768 | 3123–3426 |
| Desmocollin 2 | L33779 | 1317–1691 |
| Stat6; signal transducer and activator of transcription 6; IL-4 Stat; STA6 | L47650 | 2057–2411 |
| Lymphocyte-specific tyrosine-protein kinase LCK | M12056 | 1205–1488 |
| ERA-1 Protein (ERA-1-993) | M22115 | 723–1062 |
| Homeo Box protein 2.1 (Hox-2.1) | M26283 | 647–884 |
| Zinc finger X-chromosomal protein (ZFX) | M32309 | 2153–2554 |
| WT1; Wilms tumor protein; tumor suppressor | M55512 | 1262–1563 |
| Tristetraprolin | M57422 | 262–504 |
| Nucleobindin | M96823 | 80–357 |
| PAX-5 (B cell specific transcription factor) | M97013 | 286–629 |
| IFNgR2; interferon-gamma receptor second (beta) chain; interferon gamma receptor accessory factor-1 (AF-1) | S69336 | 832–1089 |
| Transcriptional enhancer factor 1 (TEF-1) | S74227 | 934–1233 |
| Transcription factor NFAT 1, isoform, alpha | U02079 | 1601–1910 |
| DNA-binding protein SATB1 | U05252 | 1101–1380 |
| CCHB3; calcium channel (voltage-gated; dihydropyridine-sensitive; L-type) beta-3 subunit) | U20372 | 351–639 |
| p57kip2; cdk-inhibitor kip2 (cyclin-dependent kinase inhibitor 1 B) member of the p21CIP1 Cdk inhibitor family; candidate tumor suppressor gene | U20553 | 989–1272 |
| snoN; ski-related oncogene | U36203 | 671–1006 |
| Homeo Box protein 7.1 (Hox-7.1) | X14759 | 740–992 |
| Neuronal cell surface protein F3 | X14943 | 1033–1311 |
| GATA-3 transcription factor | X55123 | 858–1125 |
| YB1 DNA binding protein | X57621 | 550–873 |
| Dipeptidyl peptidase iv | X58384 | 61–294 |
| Fli-1 ets-related proto-oncogene | X59421 | 267–623 |
| RXR-beta cis-11-retinoic acid receptor | X66224 | 1225–1477 |
| C3H cytochrome P450; Cyp1b1 | X78445 | 295–593 |
| Ubiquitin-conjugating enzyme, yeast Rad6 homologue; murine HR6B | X96859 | 51–392 |
| Relaxin | Z27088 | 51–365 |
| Transcription factor LIM-1 | Z27410 | 1673–1934 |
| DNA topoisomerase I (Top I) | D10061 | 1051–1357 |
| DNA topoisomerase II (Top II) | D12513 | 520–870 |
| GST Pi 1; glutathione S-transferase Pi 1; preadipocyte growth factor | D30687 | 62–369 |
| Glutathione S-transferase A | J03958 | 54–311 |
| Glutathione S-transferase Mu 1 | J04696 | 13–263 |
| c-Ab1 proto-oncogene | L10656 | 878–1145 |
| A-Raf proto-oncogene | M13071 | 1042–1320 |
| c-Src proto-oncogene | M17031 | 452–758 |
| Retinoic acid binding protein II cellular (CRABP-II) | M35523 | 276–571 |
| Cyclin D2 (G1/S-specific) | M83749 | 781–1074 |
| Cyclin D3 (G1/S-specific) | U43844 | 484–790 |
| 5-Hydroxytryptamine receptor [Serotonin receptor type 2 (SHT2)] | S49542 | 400–707 |
| Cyclin D1 (G1/S-specific) | S78355 | 1858–2205 |
| Pur-alpha transcriptional activator; sequence-specific ssDNA-binding protein | U02098 | 1082–1309 |
| Cdc2Sa; cdc2SMl; MPI1 (M-phase inducer phosphatase 1) | U27323 | 606–986 |
| ERCC-1; DNA excision repair protein | X07414 | 189–484 |
| c-rel proto-oncogene | X15842 | 1729–2064 |
| Inhibin alpha subunit | X69618 | 810–1117 |
| Glutathione reductase | X76341 | 115–377 |
| Insulin-like growth factor binding protein-3 (IGFBP-3) | X81581 | 474–719 |
| Cyclin A (G2/M-specific) | Z26580 | 701–1009 |
| Preproglucagon | Z46845 | 172–531 |
| NF-kB p65; NF-kappa-B transcription factor p65 subunit; rel-related polypeptide | M61909 | 101–363 |
| PKC-theta; protein kinase C theta type | D11091 | 658–957 |
| VLA-3 alpha subunit | D13867 | 288–589 |
| NADPH-cytochrome P450 reductase | D17571 | 326–605 |
| Beta-protachykinin a | D17584 | 273–523 |
| Wee1/p87; cdc2 tyrosine 15-kinase | D30743 | 1816–2159 |
| Protein tyrosine phosphatase | D83966 | 1060–1426 |
| Jun-D; c-jun-related transcription factor | J05205 | 737–964 |
| Integrin alpha 7 | L23423 | 2399–2713 |
| Gadd45; growth arrest and DNA-damage-inducible protein | L28177 | 144–434 |
| Bcl-xL apoptosis regulator (bcl-x long); BcI-2 family member | L35049 | 641–906 |
| N-myc proto-oncogene protein | X03919 | 3262–3450 |
| cAMP-dependent protein kinase type I-beta regulatory chain | M20473 | 538–750 |
| IRF1; interferon regulatory factor 1 | M21065 | 1–233 |
| HSP86; heat shock 86kD protein | M36830 | 255–551 |
| LFA-1 alpha; integrin alpha L; leukocyte adhesion glycoprotein LFA-1 alpha chain; antigen CD11A (p180) | M60778 | 1838–2050 |
| APC; Adenomatous Polyposis Coli protein | M88127 | 4127–4476 |
| Cdc2Sb; cdc2SM2; MPI2 (M-phase inducer phosphatase 2) | S93521 | 1893–2200 |
| P13-K p110; phosphatidylinositol 3-kinase catalytic subunit | U03279 | 1437–1723 |
| RSP27; heat shock 27kD protein 1 | U03560 | 245–500 |
| Csk; c-Src-kinase and negative regulator | U05247 | 645–984 |
| Fasl; Fas antigen ligand; generalized lymphoproliferation disease gene (gld) in mice | U06948 | 168–488 |
| MAPK; MAP kinase; p38 | U10871 | 465–780 |
| p19ink4; cdk4 and cdk6 inhibitor | U19597 | 228–516 |
| Elf-1 Ets family transcription factor | U19617 | 1585–1902 |
| CRAF1; TNF receptor (CD40 receptor) associated factor; TRAF- | U21050 | 1225–1466 |

TABLE 1-continued

| GENE NAME | GENBANK # | FRAGMENT LENGTH, bp (start–end) |
|---|---|---|
| related SPI3; serpin; similar to human proteinase inhibitor 6 (placental thrombin inhibitor) serine proteinase inhibitor | U25844 | 915–1230 |
| RIP cell death protein; Fas/APO-1 (CD95) interactor, contains death domain | U25995 | 1945–2223 |
| SLAP; src-like adapter protein; Eck receptor tyrosine kinase-associated | U29056 | 109–427 |
| Atm; ataxia telangiectasia murine homologue | U43678 | 8989–9170 |
| EB1 APC-binding protein | U51196 | 607–834 |
| TANK; I-TRAF; TRAF family member associated NF-kB activator | U51907 | 135–437 |
| Caspase-11; ICH-3 cysteine protease; upstream regulator of ICE | U59463 | 352–686 |
| MLHI DNA mismatch repair protein; MutL homologue | U59883 | 1037–1278 |
| Insulin-like growth factor-IA | X04480 | 183–406 |
| Cell surface glycoprotein MAC-1 alpha subunit | X07640 | 1892–2179 |
| N-ras proto-oncogene; transforming G-protein | X13664 | 548–857 |
| L-myc proto-oncogene protein | X13945 | 5287–5590 |
| CD18 antigen beta subunit (leukocyte adhesion LFA-1) (CD3, P150, 95) | X14951 | 1366–1706 |
| c-Fgr proto-oncogene | X52191 | 1305–1538 |
| Integrin alpha 4 | X53176 | 2176–2449 |
| PKC-beta; protein kinase C beta-II type | X53532 | 1712–2089 |
| HSP60; heat shock 60 kDa protein 1 (chaperonin, GroEL homologue); mitochondrial matrix protein P1 | X53584 | 1432–1691 |
| c-Cbl proto-oncogene (Adaptor protein) | X57111 | 858–1151 |
| Cdc25 phosphatase; guanine nucleotide releasing protein | X59868 | 942–1276 |
| Ezrin; Villin 2; NF-2 (merlin) related filament/plasma membrane associated protein | X60671 | 1571–1812 |
| Cyclin B1 (G2/M-specific) | X64713 | 1184–1447 |
| Integrin alpha 6 | X69902 | 261–611 |
| 5-Hydroxytryptamine (serotonin) receptor 3 | X72395 | 1422–1711 |
| Homeobox protein HOXD-3 | X73573 | 141–362 |
| Cyclin E (G1/S-specific) | X75888 | 799–1140 |
| MAPKAPK-2; MAp kinase-activated protein kinase; MAPKAP kinase 2 | X76850 | 719–987 |
| Fra-2 (fos-related antigen 2) | X83971 | 617–844 |
| Cyclin A1 (G2/M-specific) | X84311 | 656–916 |
| DCC; netrin receptor; immunoglobulin gene superfamily member; former tumor suppressor protein candidate | X85788 | 4193–4508 |
| MHR23A; Rad23 UV excision repair protein homologue; xerodemia pigmentosum group C (XPC) repair complementing protein | X92410 | 613–955 |
| MHR23B; Rad23 UV excision repair protein homologue; xeroderma pigmentosum group C (XPC) repair complementing protein | X92411 | 542–807 |
| Integrin beta | Y00769 | 1990–2320 |
| MmRad52; yeast DNA repair protein Rad52 homologue | Z32767 | 159–417 |
| Cyclin G-(G2/M-specific) | Z37110 | 300–619 |
| Prostaglandin E2 receptor EP4 subtype | D13458 | 1146–1442 |
| Interleukin-5 receptor | D90205 | 1389–1739 |
| Epidermal growth factor (EGF) | J00380 | 180–505 |
| Erythropoietin receptor | J04843 | 1193–1377 |
| Insulin receptor | J05149 | 653–1011 |
| p53; tumor suppressor; DNA-binding protein | K01700 | 1125–1517 |
| Cf2r; coagulation factor II (thrombin) receptor | L03529 | 762–1154 |
| PTPRG; protein-tyrosine phosphatase gamma | L09562 | 1248–1504 |
| DNA-binding protein SMBP2 | L10075 | 4790–5088 |
| Interleukin-10 receptor | L12120 | 1762–2110 |
| Interleukin-2 receptor gamma chain | L20048 | 1073–1313 |
| Bone morphogenetic protein 1 | L24755 | 2402–2676 |
| Uromodulin | L33406 | 1809–2136 |
| Thrombopoietin | L34169 | 652–954 |
| Transforming growth factor beta | M13177 | 772–1075 |
| Granulocyte colony-stimulating factor (G-CSF) | M13926 | 86–377 |
| Neuroleukin | M14220 | 1110–1490 |
| Insulin-like growth factor-2 (somatomedin A) | M14951 | 46–328 |
| Interleukin 1 beta | M15131 | 827–1225 |
| c-myb proto-oncogene protein | M16449 | 1212–1513 |
| Tumor necrosis factor beta TNF-beta (Lymphotoxin-alpha) | M16819 | 461–805 |
| Interleukin-1 receptor | M20658 | 2050–2410 |
| CSF-1; M-CSF; colony stimulating factor-1 | X05010 | 1268–1657 |
| Interleukin-4 receptor (membrane-bound form) | M27959 | 2469–2705 |
| Interferon-gamma receptor | M28233 | 1262–1550 |
| Interleukin-7 receptor | M29697 | 701–1104 |
| Gamma interferon induced monokine (MIG) | M34815 | 42–323 |
| Interleukin 10 | M37897 | 175–456 |
| NF-kappa B binding subunit (nuclear factor) (TFDB5) | M57999 | 3122–3417 |
| Tumor necrosis factor receptor 1; TNFR-1 | M59378 | 1961–2376 |
| PDGFRa; platelet-derived growth factor alpha-receptor | M84607 | 474–803 |
| Interleukin-9 receptor | M84746 | 795–1086 |
| iNOS1; nitric oxide synthase (inducible) | M87039 | 3178–3455 |
| Interferon alpha-beta receptor | M89641 | 808–1120 |
| Activating transcription factor 4 (mATF4) | M94087 | 416–769 |
| Beta2-RAR; retinoic acid receptor beta-2 | S56660 | 589–896 |
| Tie-2 proto-oncogene | S67051 | 1843–2179 |
| IGF-I-R alpha; insulin-like growth factor I receptor alpha subunit | U00182 | 489–885 |
| IGFR II; insulin-like growth factor receptor II, cation-independent mannose-6-P receptor; elevated in Wilms's tumor cells | U04710 | 707–1060 |
| Stat3; APRF; acute phase response factor | U06922 | 1575–1910 |
| Calcitonin receptor 1b | U18542 | 1375–1630 |
| Endothelin b receptor [Ednrb] | U32329 | 379–695 |
| Prepro-endothelin-3 | U32330 | 703–1008 |
| Pre-platelet-derived growth factor receptor | X04367 | 2336–2677 |
| CD 4 receptor (T cell activation antigene) | X04836 | 1652–1877 |
| Interleukin 7 | X07962 | 241–496 |
| Macrophage inflamatory protein | X12531 | 25–359 |
| Thrombomodulin | X14432 | 1082–1365 |
| Interleukin 6 (B cell differentiation factor) | X51975 | 1638–1898 |
| Androgen receptor | X53779 | 2189–2491 |
| Bone morphogenetic protein 4 (BMP-4) (TGF-beta family) | X56848 | 1275–1513 |
| Transferrin receptor protein (p90, CD71) | X57349 | 654–1023 |
| Transforming growth factor beta 2 | X57413 | 2227–2541 |
| Glutamate receptor, ionotropic AMPAI | X57497 | 1290–1657 |

TABLE 1-continued

| GENE NAME | GENBANK # | FRAGMENT LENGTH, bp (start–end) |
|---|---|---|
| TNF 55; tumor necrosis factor 1 (55kd) | X57796 | 656–1022 |
| Mdm2; pS3-regulating protein | X58876 | 1364–1646 |
| Transcription factor 1 for heat shock gene | X61753 | 203–570 |
| CD40L; CD40 ligand | X65453 | 545–809 |
| c-Fms proto-oncogene (macrophage colony stimulating factor 1 (CSF-1) receptor) | X68932 | 2399–2686 |
| B-myb proto-oncogene; myb-related protein B | X70472 | 2109–2456 |
| Ear-2; v-erbA related proto-oncogene | X76654 | 1065–1376 |
| Tie-1 tyrosine-protein kinase receptor | X80764 | 1425–1844 |
| Glutamate receptor, ionotropic NMDA2B (epsilon 2) | D10651 | 506–786 |
| Glutamate receptor, ionotropic NMDA2A (epsilon 1) | D10217 | 3966–4209 |
| CD7 antigen | D10329 | 28–421 |
| Transcription factor S-II (transcription elongation factor) | D00926 | 518–767 |
| Basic Fibroblast growth factor (b-FGF) | D12482 | 290–620 |
| Bone morphogenetic protein receptor | D16250 | 1454–1837 |
| G-protein-coupled receptor | D17292 | 833–1115 |
| Transcription factor SP2 | D17407 | 734–1079 |
| CdkS; cyclin-dependent kinase 5 | D29678 | 552–882 |
| TGF-beta receptor type 1 | D25540 | 1407–1629 |
| Kinesin like protein KIF 3B | D26077 | 3519–3722 |
| Kinesin family protein KIF1A | D29951 | 2553–2830 |
| Fibroblast growth factor 9 | D38258 | 91–379 |
| Neuronal death protein | D83698 | 627–805 |
| Syp; SR-PTP2; adaptor protein tyrosine phosphatase | D84372 | 1229–1543 |
| Interferon regulatory factor 2 (IRF 2) | J03168 | 718–976 |
| Lamimin receptor 1 | J02870 | 368–675 |
| NF-IB protein (transcription factor) | D90176 | 452–791 |
| Jun-B; c-jun-related transcription factor | J03236 | 514–740 |
| Tissue plasminogen activator | J03520 | 622–1020 |
| Romeo Box protein 4.2 (Rox-4.2) | J03770 | 565–945 |
| Nur77 early response protein; thyroid hormone (TR3) receptor | J04113 | 825–1059 |
| Ets-2 transcription factor | J04103 | 917–1281 |
| c-Jun proto-oncogene (transcription factor AP-1 component) | J04115 | 951–1238 |
| Serine protease inhibitor homolog J6 | J05609 | 581–855 |
| Nerve growth factor beta (beta-NGF) | K01759 | 642–901 |
| Cdk4; cyclin-dependent kinase 4 | L01640 | 230–616 |
| Acetylcholine receptor delta subunit | K02582 | 1400–1655 |
| MAPKK1; MAP kinase kinase 3 (dual specificity) (MKK1) | L02526 | 1284–1583 |
| GABA-A transporter 4 | L04662 | 960–1341 |
| GABA-A transporter 3 | L04663 | 1010–1320 |
| Vegfr1; Vascular endothelial growth factor receptor 1/Fms-related tyrosine kinase 1 (Flt1) | L07297 | 1144–1541 |
| Adrenergic receptor, beta 1 | L10084 | 404–772 |
| Eph3 (Nuk) tyrosine-protein kinase receptor | L25890 | 2255–2491 |
| MTJ1; DnaJ-like heat-shock protein from mouse tumor | L16953 | 1059–1384 |
| TTMP-3 tissue inhibitor of metalloproteinases-3 | L19622 | 274–592 |
| Insulin receptor substrate-1 (IRS-1) | L24563 | 1027–1304 |
| YY1 (UCRBP) transcriptional factor | L13968 | 1052–1292 |
| Interleukin-converting enzyme (TCE) | L28095 | 30–269 |
| Hepatoma transmembrane kinase ligand | L38847 | 927–1219 |
| Voltage-gated sodium channel | L36179 | 4179–4505 |
| Bad; heterodimeric partner for Bcl-XL and Bcl-2; promotes cell death | L37296 | 1079–1375 |
| Jnk stress-activated protein kinase (SAPK) | L35236 | 795–1032 |
| Cytoskeletal epidermal keratin (18 human) | M11686 | 473–773 |
| Nerve growth factor alpha (alpha-NGF) | M11434 | 294–494 |
| Epidermal keratin (1 human) | M10937 | 326–683 |
| Nicotinic acetylcholine receptor | M14537 | 1226–1568 |
| MDR1; P-glycoprotein; multidrug resistance protein; efflux pump | M14757 | 1500–1886 |
| CD2 antigen | M18934 | 354–602 |
| Homeo Box protein 1.1 (Hox-1.1) | M17192 | 466–723 |
| Fetal myosin alkali light chain | M19436 | 205–504 |
| Interleukin 4 | M25892 | 77–310 |
| Rb; pp105; Retinoblastoma susceptibility-associated protein (tumor suppressor gene; cell cycle regulator) | M26391 | 2036–2296 |
| Rsk; ribosomal protein S6 kinase | M28489 | 1191–1436 |
| Pletelet- derived growth factor (A chain) (PDGF- A) | M29464 | 152–425 |
| Cytoskeletal epidermal keratin (19 human) | M28698 | 194–500 |
| RAG-1; V(D)J recombination activating protein | M29475 | 2155–2404 |
| Interleukin-3 receptor | M29855 | 1975–2254 |
| K-fibroblast growth factor | M30642 | 309–577 |
| Octamer binding transcription factor (Oct 3) | M34381 | 774–999 |
| Plasminogen activator inhibitor | M33960 | 1096–1344 |
| CD3 antigen, delta polypeptide | M33158 | 73–361 |
| Homeo Box protein 2.5 (Hox-2.5) | M34857 | 11–277 |
| HSP84; heat shock 84kD protein | M36829 | 342–736 |
| Mast cell protease (MMCP) - 4 | M55617 | 634–992 |
| Erk1; extracellular signal-regulated kinase 1; p44; Ert2 | M61177 | 115–373 |
| P13-K p85; phosphatidylinositol 3-kinase regulatory subunit; phosphoprotein p85; PDGF signaling pathway member | M60651 | 981–1260 |
| p58/GTA; galactosyltransferase associated protein kinase (cdc2-related protein kinase) | M58633 | 1022–1284 |
| Serine protease inhibitor 2 (spi-2) | M64086 | 1499–1754 |
| B-Raf proto-oncogene | M64429 | 1651–2036 |
| Etkl (Mek4; HEK) tyrosine-protein kinase receptor HEK | M68513 | 2681–2915 |
| RAG-2; V(D)J recombination activating protein | M64796 | 671–944 |
| Collagenase type IV | M84324 | 696–1040 |
| Interleukin-6 receptor beta chain; membrane glycoprotein gp130 | M83336 | 1423–1741 |
| Alpha cardiac myosin heavy chain | M76601 | 2094–2391 |
| Retinoic acid receptor RXR- gamma | M84819 | 701–1082 |
| Granulocyte-macrophage colony-stimulating factor receptor. | M85078 | 904–1289 |
| GABA-A receptor alpha-1 submit | M86566 | 1251–1606 |
| Endothelial ligand for L-selectin (GLYCAM 1) | M93428 | 182–541 |
| Integrin beta 7 subunit | M95633 | 2142–2423 |
| DNAse I | U00478 | 665–871 |
| Cortactin; protein tyrosine kinase substrate | U03184 | 426–653 |
| Adenosine A2M2 receptor | U05672 | 491–735 |
| DNA ligase I | U04674 | 1678–2054 |
| Adenosine A1M receptor | U05671 | 302–673 |
| Non-muscle myosin light chain 3 | U04443 | 84–370 |
| Cathepsin H | U06119 | 325–694 |
| Stat1; signal transducer and activator of transcription | U06924 | 1749–2104 |
| p21/Cip1/Waf1; cdk-inhibitor protein | U09507 | 9–403 |
| Cdk7; MO15; cyclin-dependent kinase 7 (homologue of Xenopus MO15 cdk-activating kinase) | U11822 | 454–824 |
| p27kipl; G1 cyclin-Cdk protein kinase inhibitor, p21-related | U10440 | 270–454 |
| Gem; induced, immediate early | U10551 | 220–471 |

TABLE 1-continued

| GENE NAME | GENBANK # | FRAGMENT LENGTH, bp (start–end) |
|---|---|---|
| protein; Ras family member | | |
| VRL; Von Hippel-Lindau tumor suppressor protein | U12570 | 885–1111 |
| Cek 5 receptor protein tyrosine kinase ligand | U12983 | 1037–1287 |
| Glutathione peroxidase (plasma protein); selenoprotein. | U13705 | 766–1046 |
| Integrin alpha 5 (CD51) | U14135 | 2170–2516 |
| Ski proto-oncogene | U14173 | 707–1037 |
| Ablphilin-I (abi-1) similar to HOXD3 | U17698 | 351–585 |
| BAG-1; bcl-2 binding protein with anti-cell death activity | U17162 | 17–334 |
| Shc transforming adaptor protein; Src homology 2 (SR2) protein, SRB-related | U15784 | 1220–1451 |
| MAPKK4; MAP kinase kinase 4; Jnk activating kinase 1; (JNKK1; SEK1; MKK4) | U18310 | 1380–1749 |
| Transcription factor LRG - 21 | U19118 | 618–966 |
| Interferon inducible protein 1 | U19119 | 1342–1636 |
| A20 zinc finger protein; apoptosis inhibitor | U19463 | 1952–2293 |
| p18ink4; cdk4 and cdk6 inhibitor | U19596 | 16–284 |
| I-kB (I-kappa B) beta | U19799 | 419–778 |
| Dv12; dishevelled-2 tissue polarity protein | U24160 | 1205–1578 |
| Nuclear factor related to P45 NF-E2 | U20532 | 1429–1759 |
| MSH2 DNA mismatch repair protein; MutS homologue 2 | U21011 | 2150–2490 |
| GapIII; GTPase-activating protein | U20238 | 328–644 |
| Syk tyrosine-protein kinase (activated p21cdc42Rs kinase (ack)) | U25685 | 1235–1524 |
| p107; RBL1; Retinoblastoma gene product-related protein p107 (cell cycle regulator) | U27177 | 1973–2365 |
| PMS2 DNA mismatch repair protein; yeast PMSI homolog 2 | U28724 | 749–1013 |
| Limphotoxin receptor (TNFR family) | U29173 | 1415–1668 |
| BRCA1; Breast/ovarian cancer susceptibility locus 1 product | U31625 | 5126–5430 |
| Pm1; Murine homologue of the leukemia-associated PML gene | U33626 | 1667–2064 |
| Transducin beta-2 subunit | U34960 | 515–834 |
| I-kB (I-kappa B) alpha chain | U36277 | 541–823 |
| TRAIL; TNF-related apoptosis inducing ligand; Apo-2 ligand | U37522 | 981–1288 |
| p130; Retinoblastoma gene product-related protein Rb2/p130 (cell cycle regulator) | U36799 | 970–1321 |
| CACCC Box- binding protein BKLF | U36340 | 826–1065 |
| FAF1; Fas-associated protein factor, apoptosis activator | U39643 | 423–681 |
| Zinc finger transcription factor RU49 | U41671 | 1229–1591 |
| GTBP; G/T-mismatch binding protein; MSH6. | U42190 | 1477–1769 |
| PLC beta; phospholipase C beta 3 | U43144 | 1933–2271 |
| Frizzled-3; Drosophila tissue polarity gene frizzled homologue 3; dishevelled receptor | U43205 | 2037–2285 |
| MAPKK3; MAP kinase kinase 3 (dual specificity) (MKK3, MEK3) | U43187 | 1436–1742 |
| Myeloblastin; trypsin-chymotrypsin related serine protease | U43525 | 503–807 |
| Zinc finger Kruppel type Zfp 92 | U47104 | 578–896 |
| TDAG51; couples TCR signaling to Fas (CD95) expression | U44088 | 729–1042 |
| POU domain, class 2, associated factor 1 | U43788 | 610–884 |
| ALG-2; calcium binding protein required for programmed cell death | U49112 | 527–861 |
| Unconventional myosin VI | U49739 | 3784–4021 |
| Transcription factor CTCF (11 zinc fingers) | U51037 | 1625–1911 |
| Transcription factor C 1 | U53925 | 3895–4227 |
| Madrl; mSmadl; Mothers against dpp protein (Mad) murine homologue; TGF-beta signaling protein-1 (bsp-1); candidate tumor suppressor gene | U58992 | 238–476 |
| Bcl-W apoptosis regulator; Bcl-2 family member | U59746 | 153–368 |
| Mad related protein 2 (MADR2) | U60530 | 584–820 |
| Cyclin C (G1-specific) | U62638 | 714–986 |
| Mph-1 nuclear transcriptional repressor for hox genes | U63386 | 1621–1884 |
| Rad50; DNA repair protein | U66887 | 1383–1707 |
| Fyn proto-oncogene; Src family member | U70324 | 584–882 |
| c-myc proto-oncogene protein | X01023 | 379–667 |
| c-Fos proto-oncogene; transcription factor AP-1 component fos cellular oncogene | V00727 | 482–734 |
| Cathepsin L | X06086 | 267–588 |
| Glutamate receptor channel subunit gamma | X04648 | 41–408 |
| c-Fes proto-oncogene | X12616 | 2342–2598 |
| Cytotoxic cell protease 2 (B10) | X12822 | 439–686 |
| Homeo Box protein 3.1 (Hox-3.1) | X07439 | 449–722 |
| Homeo Box protein 2.4 (Hox-2.4) | X13721 | 1949–2284 |
| Fos-B; c-fos-related protein fos B | X14897 | 920–1278 |
| Plasminogen activator inhibitor-2 | X16490 | 674–978 |
| c-ErbA oncogene; thyroid hormone receptor. | X51983 | 400–675 |
| Cathepsin D | X53337 | 587–894 |
| Vimentin | X51438 | 868–1096 |
| HMG-14 non histone chromosomal protein | X53476 | 643–1017 |
| Macrophage inflamatory protein 2 alpha (MIP 2 alpha) | X53798 | 14–352 |
| Bone morphogenetic protein 7 (BMP-7) (osteogenic protein 1) | X56906 | 670–971 |
| Transcription factor SP1P (POUdomain transcription factor) | X56959 | 866–1128 |
| Homeo Box protein 8 (Hox-8) | X59252 | 826–1132 |
| Fibroblast growth factor receptor 4 | X59927 | 2446–2820 |
| Rac1 murine homologue | X57277 | 425–651 |
| Transcription factor UBF | X60831 | 689993 |
| Kinesin heavy chain | X61435 | 1898–2182 |
| CCAAT- Binding transcription factor(C/EBP) | X61800 | 904–1150 |
| TIMP-2 tissue inhibitor of metalloproteinases-2 | X62622 | 1236–1468 |
| Ets-related protein PEA 3 | X63190 | 1702–2040 |
| Vav; GDP-GTP exchange factor; proto-oncogene | X64361 | 1083–1351 |
| PAX-6 (paired box protein) | X63963 | 1081–1325 |
| Cyclin B2 (G2/M-specific) | X66032 | 874–1236 |
| Chop10; murine homologue of Gadd153 (growth arrest and DNA-damage-inducible protein) | X67083 | 17–332 |
| PD-1 possible cell death inducer; Ig gene superfamily member | X67914 | 1481–1734 |
| Inhibin beta A subunit (TGF beta family) | X69619 | 1064–1304 |
| Vegfr2; KDR/flk1 vascular endothelial growth factor tyrosine kinase receptor | X70842 | 1394–1721 |
| Protease nexin 1 (PN-1) | X70296 | 746–985 |
| MRE-binding transcription factor | X71327 | 552–916 |
| Activator-1 140 KD subunit (replication factor C 140KD) | X72711 | 4137–4375 |
| DP-1 (DRTF-polipeptide 1) cell cycle regulatory transcription factor | X72310 | 925–1305 |
| 5-Hydroxytryptamine (serotonin) receptor 1c | X72230 | 982–1314 |
| Gelatinase B | X72795 | 599–954 |
| XPAC; xeroderma pigmentosum group A correcting protein | X74351 | 447–669 |

TABLE 1-continued

| GENE NAME | GENBANK # | FRAGMENT LENGTH, bp (start–end) |
|---|---|---|
| Integrin alpha 2 (CD49b) | X75427 | 1595–1976 |
| Growth/diffferentiation factor 2 (GDF-2) | X77113 | 939–1329 |
| Insulin-like growth factor binding protein-4 (IGFBP-4) | X81582 | 781–1140 |
| Insulin-like growth factor binding protein-1 (IGFBP-1) | X81579 | 27–256 |
| IGFBP-2; Insulin-like growth factor binding protein 2; autocrine and/or paracrine growth promoter | X81580 | 449–817 |
| Insulin-like growth factor binding protein-5 (IGFBP-5) | X81583 | 461–824 |
| Insulin-like growth factor binding protein-6 (IGFBP 6) | X81584 | 701–1039 |
| A-myb proto-oncogene; myb-related protein A | X82327 | 1017–1334 |
| Membrane type matrix matalloproteinase | X83536 | 877–1101 |
| Elk-1 ets-related proto-oncogene | X87257 | 1498–1680 |
| E2F-5 transcription factor | X86925 | 426–728 |
| Lbx 1 transcription factor | X90829 | 1000–1306 |
| P-selectin (glycoprotein ligand-1) | X91144 | 1095–1323 |
| Transcription factor SEF2 | X91753 | 755–1054 |
| Macrophage mannose receptor | Z11974 | 807–1197 |
| Rab-2 ras-related protein | X95403 | 232–505 |
| Gluthathione S-transferase (theta type1); phase II conjugation enzyme | X98055 | 14–298 |
| Zyxin; LIM domain protein; alpha-actinin binding protein | X99063 | 1437–1812 |
| Met protooncogene | Y00671 | 3646–3933 |
| c-Kit proto-oncogene (mast/stem cell growth factor receptor tyrosine kinase) | Y00864 | 2867–3181 |
| Transcription factor BARX1 (homeodian transcription factor) | Y07960 | 723–973 |
| PLC gamma; phospholipase C gamma | X95346 | 180–516 |
| Stromelysin-3: matrix metalloproteinase-11 (MMP-11) | Z12604 | 1463–1806 |
| 5-Hydroxytryptamine (serotonin) receptor 1e beta | Z14224 | 530–774 |
| 5-Hydroxytryptamine (serotonin) receptor 2c | Z15119 | 588–940 |
| Low density lipoprotein receptor | Z19521 | 1047–1324 |
| 5-Hydroxytryptamine (serotonin) receptor 7 | Z23107 | 460–817 |
| c-Mpl; thrombopoietin receptor; mematopoietic growth factor receptor superfamily member | Z22649 | 1561–1772 |
| DNA-polymerase delta catalytic subunit | Z21848 | 1256–1600 |
| Follistatin | Z29532 | 764–1053 |
| Cyclin F (S/G2/M-specific) | Z47766 | 2431–2708 |
| Ets-related protein Sap 1A | Z26885 | 1267–1521 |
| Net; ets related transcription factor; activated by Ras | Z32815 | 1211–1595 |
| Stat5a; mammary gland factor | Z48538 | 2269–2628 |
| Hek2 murine homologue; Mdk5 mouse developmental kinase; Eph - related tyrosine-protein kinase receptor | Z49086 | 1702–1930 |
| D-Factor/LIF receptor | D26177 | 2376–2775 |
| Cytoskeletal epidermal keratin (14 human) | M13806 | 108–469 |
| R-ras protein, closely related to ras proto-oncogenes | M21019 | 215–555 |
| Prolactin receptor PRLR2 | M22959 | 1–328 |
| Blk; B lymphocyte kinase; Src family member | M30903 | 1307–1672 |
| Macrophage inflammatory protein 1 beta (Act 2) | M35590 | 119–445 |
| Alpha-1 protease inhibitor 2 GABA-A transporter 1 | M75716 | 625–969 |
| Bone morphogenetic protein 8a (BMP-8a)(TGF-beta family) | M97017 | 788–1139 |
| Erythroid kruppel-like transcription factor | M97200 | 783–1171 |
| GATA binding transcription factor (GATA-4) | M98339 | 81–379 |
| Growth factor receptor | M98547 | 1701–2014 |
| Crk adaptor protein | S72408 | 750–1027 |
| Retinoid X receptor interacting protein (RIP 15) | U09419 | 1388–1682 |
| Cek 7 receptor protein tyrosine kinase ligand | U14752 | 504–837 |
| C-C CKR-1; CCR-1; C-C chemokine receptor type 1, macrophage inflammatory protein-1 alpha receptor; MIP-1alpha-R; RANTES-R | U29678 | 168–495 |
| Glucocorticoid receptor form A | X13358 | 1527–1816 |
| Mothers against DPP protein (mad homolog Smad 1, transforming growth factor beta signaling protein) | X83106 | 464–728 |
| Hck tyrosine-protein kinase | Y00487 | 1308–1563 |
| Photolysase/blue-light receptor homologue | AB000777 | 1418–1737 |
| Osp94 osmotic stress protein; APG-1; hsp70-related | D49482 | 1026–1266 |
| Glucose regulated protein, 78kD; Grp78 | D78645 | 167–411 |
| LCR-1; CXCR-4; CXC(SDF-1) chemokine receptor 4; HIV coreceptor (fusin); G protein-coupled receptor LCR1 homologue; | D87747 | 584–867 |
| Glucose transporter-1, erythrocyte; Glut1 | M23384 | 325–653 |
| Int-3 proto-oncogene; NOTCH family member; NOTCH4 | M80456 | 1846–2145 |
| c-Akt proto-oncogene; Rac-alpha; proteine kinase B (PKB) | M94335 | 604–899 |
| Bak apoptosis regulator; Bcl-2 family member | Y13231 | 1509–1786 |
| PS-2; homologue of the Alzheimer's disease gene | U57324 | 437–783 |
| BRCA2; Breast cancer susceptibility locus 2 product | U65594 | 649–922 |
| DNA ligase III | U66058 | 2980–3205 |
| Caspase-7; Lice2; ICE-LAP3 cysteine protease | U67321 | 1040–1280 |
| BID; apoptic death agonist | U75506 | 452–777 |
| WBP6; pSK-SRPK1; WW domain binding protein 6 serine kinase for SR splicing factors | U92456 | 482–774 |
| Cyclin G2 (G2/M-specific) | U95826 | 408–688 |
| Ung1; uracil-DNA glycosylase | X99018 | 444–729 |
| Rab-3b ras related protein | Y14019 | 232–562 |
| Inhibitor of the RNA-activated protein kinase, 58-kDa | U28423 | 180–487 |
| Golgi 4-transmembrane spanning transporter; MTP | U34259 | 742–1060 |
| ATP-binding casette 8; ABC8; homolog of Drosophila white | U34920 | 1011–1319 |
| CDC42 GTP-binding protein; G25K | U37720 | 1675–1982 |
| Etoposide induced p53 responsive (Et24) mRNA | U41751 | 1041–1296 |
| Casein kinase II (alpha subunit) | U51866 | 1237–1517 |
| TSG101 tumor susceptibility protein | U52945 | 446–713 |
| Tumor suppressor maspin | U54705 | 251–507 |
| FLIP-L, apoptosis inhibitor; FLICE-like inhibitory protein | U97076 | 1476–1811 |
| CamK II; Ca2+/calmodulin-dependent protein kinase II (beta subunit) | X63615 | 1951–2219 |
| Htk; Mdk2 mouse developmental kinase; Eph-related tyrosine-protein kinase receptor | Z49085 | 2032–2365 |
| Glial cell line-derived neurotrophic factor | D49921 | 236–539 |
| CD31 (Platelet endothelial cell adhesion molecule 1) | L06039 | 1172–1494 |

TABLE 1-continued

| GENE NAME | GENBANK # | FRAGMENT LENGTH, bp (start–end) |
|---|---|---|
| CD22 antigen | L16928 | 2314–2645 |
| Gbx 2 | L39970 | 1122–1395 |
| Cytotoxic T lymphocyte-specific serine protease CCP I gene (CTLA-1) | M12302 | 585–830 |
| Cathepsin B | M14222 | 384–729 |
| Growth hormone receptor | M33324 | 1924–2240 |
| CD28 (receptor for B71) | M34563 | 544–774 |
| Estrogen receptor | M38651 | 742–1013 |
| Monotype chemoattractant protein 3 | S71251 | 201–491 |
| CD45 associated protein (CD 45-ap, LSM-1) | U03856 | 620–898 |
| Orphan receptor | U11688 | 1686–1943 |
| Cannabinoid receptor 1 (brain) | U17985 | 1091–1437 |
| Dystrogycan 1 | U43512 | 2267–2505 |
| G-protein coupled receptor | U46923 | 350–671 |
| Urokinase type plasminogen activator | X02389 | 1301–1538 |
| CTLA-4 (immunoglobin superfamily member) | X05719 | 246–519 |
| Myogenic factor 5 | X56182 | 232–528 |
| uPAR1; urokinase plasminogen activator surface receptor (CD87) | X62700 | 482–756 |
| Serine protease inhibitor 2.4 | X69832 | 621–927 |
| SRY-box containing gene 4 | X70298 | 34–311 |
| Bone morphogenetic protein 2 (BMP-2)(TGF-beta family) | L25602 | 8372–8724 |
| [K02588]P-1-450; dioxin-inducible cytochrome P450 | M10021 [K02588] | 3729–4014 |
| Bcl-2; B cell lymphoma protein 2, apoptosis inhibitor | M16506 | 2125–2367 |
| CD14 antigen | M34510 | 667–931 |
| Somatostatin receptor 2 | M81832 | 47–310 |
| Dopamine receptor 4 | U19880 | 907–1191 |
| Cannabinoid receptor 2 (macrophage, CB2) | U21681 | 910–1262 |
| Erf(Ets-related transcription factor) | U58533 | 1286–1613 |
| 5-Hydroxytryptamine (serotonin) receptor 1b | Z11597 | 1043–1355 |
| Tob antoproliferative factor; interacts with p185erbB2 | D78382 | 540–876 |
| Gluthathione S-transferase (microsomal) | J03752 | 185–428 |
| Adensine A3 receptor | L20331 | 182–382 |
| p55cdc; cell division control protein 20 | U05341 | 1061–1348 |
| AP endonuclease; apurinic/apyrimidinic endonuclease (Apex) | U12273 | 1894–2150 |
| Mas proto-oncogene (G-protein coupled receptor) | X67735 | 566–808 |
| AT motif-binding factor ATBF1 | D26046 | 9807–10112 |
| HMG-box transcription factor from testis (MusSox17) | D49474 | 427–662 |
| Ikaros DNA binding protein | L03547 | 627–890 |
| Early B cell factor (EBF) | L12147 | 750–1026 |
| Engariled protein (En-1) homolog | L12703 | 1323–1554 |
| Engrailed protein (En-2) homolog | L12705 | 1626–1895 |
| Transcription factor A10 | L21027 | 499–806 |
| Myocyte nuclear factor (MNF) | L26507 | 1203–1456 |
| Basic domain/leucine zipper transcription factor | L36435 | 872–1073 |
| Caudal type Homeobox 1 (Cdx1) | M37163 | 1040–1301 |
| Butyrate response factor 1 | M58566 | 768–22 |
| Brain specific transcription factor NURR-1 | S53744 | 1548–1754 |
| Brn-3.2 POU transcription factor | S68377 | 877–1237 |
| Caudal type Homeobox 2 (Cdx2) | S74520 | 1085–1367 |
| Erythroid transcription factor NF-E2 | U01036 | 1–241 |
| Gut-specific Kruppel-like factor GKLF | U20344 | 1558–1789 |
| Kruppel-like factor LKLF | U25096 | 898–1193 |
| Neuronal helix-loop-helix protein NEX-1 | U29086 | 572–907 |
| Brain factor 1 (Hfhbf1) | U36760 | 1080–1318 |
| Split hand/foot gene | U41626 | 92–303 |
| Sim transcription factor | U42554 | 2828–3066 |
| Glial cells missing gene homolog (mGCM1) | U59876 | 727–1080 |
| Sp4 zinc finger transcription factor | U62522 | 1704–1929 |
| Heat shock transcription factor 2 (HSF 2) | X61754 | 1445–1640 |
| RNA polymerase I termination factor TTF-1 | X83974 | 3222–3433 |
| Hepatocyte nuclear factor 3/forkhead homolog 8 (HFH-8) | L35949 | 913–1232 |
| SRY-box containing gene 3 (Sox3) | X94125 | 212–443 |
| Cot proto-oncogene | D13759 | 696–956 |
| HR21spA; protein involved in DNA double-strand break repair; PW29; calcium-binding protein | D49429 | 103–434 |
| MmLim15; RecA-like gene; DMC1 homologue; meiosis-specific homologous recombination protein | D64107 | 581–781 |
| ERp72 endoplasmic reticulum stress protein; protein disulfide isomerase-related protein | J05186 | 1160–1470 |
| HMG1-related VDJ recombination signal binding protein | S50213 | 2263–2531 |
| Gli oncogene; zinc finger transcription factor | S65038 | 104–505 |
| Tiam-1 invasion inducing protein; GDP-GTP exchanger-related | U05245 | 4329–4628 |
| Sik; Src-related intestinal kinase | U16805 | 1246–1623 |
| Lfc proto-oncogene | U28495 | 853–1150 |
| Oxidative stress-induced protein mRNA | U40930 | 1248–1561 |
| STAM; signal transducing adaptor molecule | U43900 | 576–811 |
| ShcC adaptor; Shc-related; brain-specific | U46854 | 246–601 |
| MmMre11a putative endo/exonuclease | U58987 | 866–1204 |
| PCNA; proliferating cell nuclear antigen; processivity factor | X53068 | 53–320 |
| Translin; recombination hotspot binding protein | X81464 | 205–431 |
| PA6 stromal protein; RAG1 gene activator | X96618 | 442–749 |
| Sky proto-oncogene (Tyro3; Rse; Dtk) | U18342 | 1927–2286 |
| H-ras proto-oncogene; transforming G-protein | Z50013 | 1307–1544 |
| ERBB-2 receptor (c-neu; HER2 protein tyrosine kinase) | L47239 | 16–266 |
| ERBB-3 receptor | L47240 | 4–243 |
| Placental ribonuclease inhibitor (Angiogenin) | U22516 | 512–766 |
| myosin I | L00923 | 2578–2921 |
| Ca2+ binding protein, Cab45 | U45977 | 597–1082 |
| murine ornithine decarboxylase | M10624 | 865–1252 |

It is evident from the above results and discussion that the subject invention provides a rapid, high throughput means to simply and quickly obtain a broad-scale screening of mouse gene expression in a variety of different samples. Only simple hybridization protocols need be employed with the subject arrays, and signals can be detected using any convenient and readily available detection device. Despite their simplicity, assays conducted with the subject arrays yield a large amount of information regarding the expression of numerous different and important key mouse genes. As such, the subject mouse arrays find use in a variety of different applications.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A mouse array comprising a plurality of polynucleotide probe spots stably associated with the surface of a solid support, wherein each polynucleotide probe spot comprises a polynucleotide probe composition made up of unique polynucleotides corresponding to a key mouse gene, wherein each of said unique polynucleotides: (a) does not cross-hybridize under stringent conditions with a polynucleotide of any other polynucleotide probe composition on the array; and (b) said unique polynucleotides of said array have an average length from about 120 to 700 nt.

2. The array according to claim 1, wherein said unique polynucleotides of said array have an average length of from about 200 to 600 nt.

3. The array according to claim 1, wherein said polynucleotide probe composition comprises a population of single stranded identical polynucleotides.

4. The array according to claim 1, wherein said polynucleotide probe composition comprises a population of two different complementary single stranded polynucleotides.

5. The array according to claim 1, wherein the density of spots on said array does not exceed about 400/cm$^2$.

6. The array according to claim 1, wherein the number of polynucleotide probe spots on said array ranges from about 50 to 1000.

7. A mouse array comprising a plurality of 50 to 1000 polynucleotide probe spots stably associated with the surface of a solid support, wherein each polynucleotide probe spot comprises a polynucleotide probe composition made up of unique polynucleotides of from about 120 to 700 nt in length that do not cross-hybridize under stringent conditions with the polynucleotides of any other polynucleotide probe composition on the array and that correspond to a key mouse gene.

8. The array according to claim 7, wherein said polynucleotide probe composition comprises a population of single stranded identical polynucleotides.

9. The array according to claim 7, wherein said polynucleotide probe composition comprises a population of two different complementary single stranded polynucleotides.

10. The array according to claim 7, wherein the density of spots on said array does not exceed about 400/cm$^2$.

11. The array according to claim 7, wherein at least 10 mouse genes of Table 1 are represented on said array.

12. A mouse array comprising from about 50 to 1000 polynucleotide probe spots stably associated with the surface of a solid support and having a density that does not exceed about 500 spots/cm$^2$, wherein said plurality of polynucleotide probe spots comprises a polynucleotide probe composition made up of unique polynucleotides of from about 120 to 700 nt in average length that do not cross-hybridize under stringent conditions with the polynucleotides of any other polynucleotide probe composition on the array and all of the unique polynucleotides of said array correspond to key mouse genes, and further wherein at least 20 mouse genes listed in Table 1 are represented on said array.

13. The array according to claim 12, wherein each of said polynucleotide spots has a diameter ranging from about 10 to 5000 µm.

14. A kit for use in a hybridization assay, said kit comprising:

a mouse array according to claim 1.

15. The kit according to claim 14, wherein said kit further comprises reagents for generating a labeled target polynucleotide sample.

16. The kit according to claim 14, wherein said kit further comprises a hybridization buffer.

17. The kit according to claim 14, wherein said kit further comprises a wash medium.

* * * * *